(12) United States Patent
Matsuzawa et al.

(10) Patent No.: US 7,285,275 B2
(45) Date of Patent: Oct. 23, 2007

(54) SMOOTH MUSCLE GROWTH INHIBITORY COMPOSITION, DIAGNOSTIC METHOD FOR ARTERIOSCLEROSIS, AND KIT THEREFOR

(75) Inventors: Yuji Matsuzawa, Takarazuka (JP); Yasukazu Ohmoto, Tokushima (JP)

(73) Assignee: Otsuke Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 11/097,334

(22) Filed: Apr. 4, 2005

(65) Prior Publication Data

US 2005/0163779 A1    Jul. 28, 2005

Related U.S. Application Data

(62) Division of application No. 10/189,493, filed on Jul. 8, 2002, now abandoned, which is a division of application No. 09/530,423, filed as application No. PCT/JP98/04862 on Oct. 27, 1998, now Pat. No. 6,461,821.

(30) Foreign Application Priority Data

Oct. 29, 1997   (JP)   ................................ 9-297569

(51) Int. Cl.
*A61K 38/16*   (2006.01)
*A61K 38/27*   (2006.01)
*C07K 1/12*   (2006.01)

(52) U.S. Cl. .................................... 424/185.1; 530/359

(58) Field of Classification Search ................ 530/359; 424/185.1
See application file for complete search history.

(56) References Cited

U.S. PATENT DOCUMENTS 5,858,682 A    1/1999   Gruenwald et al.
5,869,330 A *  2/1999   Scherer et al. ............ 435/320.1

FOREIGN PATENT DOCUMENTS

JP   PCT/IPEA/409   12/1999
WO   WO96/39429     12/1996

OTHER PUBLICATIONS

Gennaro et al, in Remington's Pharmaceutical Sciences, eighteenth edition, 1990, pp. 1300-1329.*
Webster's II new Riverside University Dictionary p. 945, 1988.*
Harlow et al, in Antibodies a Laboratory Manual, 1988, Cold Spring harbor laboratory publication, Cold Spring Harbor, NY, p. 77.*
Maeda et al, *Biochem. Biophys. Res. Commun.*, 221:286-289 (1996).
Kuriyama et al, *Strides of Medicine*, 185(9):587-591 (1998).
Maeda et al, *J. of Clin. Chem.*, 34(8):1027-1033 (1998).
Stryer et al, in Biochemistry, Third edition, WH Freeman Company, New York, pp. 31-33, 1998.
Kuby, et al., 1994, Immunology, second edition, pp. 85-96.
Abaza et al, J of Protein Chemistry 11(5):433-444, 1992.
Campbell, et al in Monoclonal Antibody Technology, 1984, Elsevier Science Publisher, NY, NY pp. 1-32.

* cited by examiner

*Primary Examiner*—Christina Chan
*Assistant Examiner*—Phuong Huynh
(74) *Attorney, Agent, or Firm*—Sughrue Mion, PLLC

(57) ABSTRACT

The invention provides not only a smooth muscle growth inhibitory composition and a composition for inhibiting expression of adhesion molecules in vascular endothelial cells, each comprising the adipose tissue-specific secretory factor apM1 as an active ingredient, but also a method for diagnosis of arteriosclerosis which comprises assaying apM1 in a sample, an antibody against apM1, and a diagnostic kit for arteriosclerosis which comprises the antibody as an active component, all of which contribute to the elucidation of obesity-related genes and corresponding expression products which are useful for the etiologic exploration and establishment of therapeutic modalities for various obesity-related diseases, particularly arteriosclerosis inclusive of angina pectoris and myocardial infarction. By utilizing the information thus obtained, therapeutic and diagnostic methods for various diseases can be established.

8 Claims, 5 Drawing Sheets

SMOOTH MUSCLE GROWTH INHIBITORY COMPOSITION, DIAGNOSTIC METHOD FOR ARTERIOSCLEROSIS, AND KIT THEREFOR

This is a divisional of application Ser. No. 10/189,493 filed Jul. 8, 2002, now abandoned, and which is a Divisional Application of application Ser. No. 09/530,423, filed May 1, 2000, now U.S. Pat. No. 6,461,821, and which is a 371 of PCT/JP98/04862 filed Oct. 27, 1998.

TECHNICAL FIELD

This invention relates to a smooth muscle growth inhibitory composition comprising apM1 (adipose most abundant gene transcript 1) as an active ingredient, a method for diagnosis of arteriosclerosis (atherosclerosis) which comprises assaying said apM1 in a sample, and a diagnostic kit for arteriosclerosis which comprises an antibody against said apM1 as an active component.

BACKGROUND ART

It is well known that, in modern society, obesity or an excessive accumulation of body fat is involved in the development of diabetes mellitus, hyperlipidemia, hypertension, and atherosclerotic diseases inclusive of angina pectoris and myocardial infarction. With obesity, not only genetic factors but also environmental factors are associated.

Recently, leptin and many other obesity-related genes have been isolated from animal models. While the group of these genes thus isolated is suspected to be involved in the establishment of obesity in man, various environmental factors such as the excessive food intake and insufficient physical exercise by contemporary man are also considered to be playing a crucial role in the development of diabetes mellitus and atherosclerosis via fat storage.

Not only the search for obesity-related genes but also the approach toward elucidation of the specific genes expressed in adipose tissues under overnutrition and of the influences of such gene transcripts on the individual seem to be of remarkable significance for expatiation of the etiologies of said diseases and establishment of relevant therapeutic modalities.

The object of this invention is to cast light on the obesity-related genes and their expression products which should be useful for elucidation of the pathogenesis of various obesity-related diseases, particularly atherosclerotic diseases such as angina pectoris, myocardial infarction, etc., and establishment of pertinent therapeutic modalities and to establish therapeutic and diagnostic methods for the diseases by utilizing such genes and expression products.

The inventors have conducted intensive studies for accomplishing the above object and made it clear previously that accumulation of fat, particularly visceral fat in the abdominal cavity, is closely associated with abnormal glucose tolerance, hyperlipidemia and hypertension. Furthermore, through large-scale sequencing analyses of the genes expressed in adipose tissue, they elucidated that many secretory protein genes have been expressed in adipose tissue and that, particularly in visceral fat, the expression of various bioactive substance genes can be observed. In addition to the cloning of those known genes, the inventors succeeded in cloning an adipose tissue-specific collagen-like protein apM1 gene [Biochem. Biophys. Res. Commun., 221, 286-289 (1996)].

This apM1 gene was found to be coding for the secretory protein (apM1) consisting of 244 amino acid residues, contain a 66-residue collagen-like motif (G-X-Y), and have homology with the C1q subcomponent of the complement system and collagen X and VII. However, the physiological function of this gene and its expression product apM1 remained to be known.

In the ensuring research, the inventors made a series of investigations in regard to the expression of said apM1 gene by the genetic engineering technique, preparation of an antibody against the expression product apM1, establishment of an apM1 assay system utilizing said antibody, and relationship of the blood apM1 concentration determined by using said assay system to the body fat distribution or various diseases. The research led to the novel finding, inter alia, that apM1 has smooth muscle growth inhibitory activity and that the blood apM1 concentration faithfully reflects the atherosclerotic change.

Furthermore, the inventors obtained the novel finding that apM1 is effective in the prevention and treatment of post-angioplasty restenoses, such as restenosis after percutaneous transluminal coronary angioplasty (PTCA) using a stent, and for that matter, in the prophylaxis and therapy of atherosclerotic diseases accompanied by angiopathy, such as angina pectoris and myocardial infarction. This invention has been developed on the basis of the above finding.

DISCLOSURE OF INVENTION

In accordance with the invention, there is provided a smooth muscle growth inhibitory composition comprising a pharmacologically effective amount of at least one member selected from the group consisting of apM1 and its salt in combination with a pharmaceutically acceptable carrier.

Furthermore, in accordance with the invention, there is provided a therapeutic and prophylactic composition for post-angioplasty restenoses which comprises a pharmacologically effective amount of at least one member selected from the group consisting of apM1 and its salt in combination with a pharmaceutically acceptable carrier.

There is also provided in accordance with the invention a prophylactic and therapeutic composition for arteriosclerosis which comprises a pharmacologically effective amount of at least one member selected from the group consisting of apM1 and its salt in combination with a pharmaceutically acceptable carrier.

There is also provided in accordance with the invention a method for diagnosis of arteriosclerosis which comprises quantitating apM1 in a sample with an anti-apM1 antibody and comparing the value thus found with the values measured in healthy subjects and in patients with arteriosclerosis.

In addition, the present invention provides a diagnostic kit for arteriosclerosis, which comprises an anti-apM1 antibody as an active component, and a monoclonal anti-apM1 antibody which is effective in diagnosing the arteriosclerosis.

The smooth muscle growth inhibitory composition according to the invention is effective, through its smooth muscle growth inhibitory activity, in the prophylaxis and therapy of atherosclerotic diseases accompanied by angiopathy, such as angina pectoris, myocardial infarction inclusive of thrombosis, brain infarction, etc. and in the arrest of progression of such atherosclerotic diseases. In fact, apM1 as the active ingredient of the composition of the invention has an ability to inhibit expression of the cell adhesion molecules governing the onset of arteriosclerosis, namely VCAM-1 (vascular cell adhesion molecule-1), ELAM (endothelial leukocyte adhesion molecule), ICAM-1 (intercellular adhesion molecule-1), and so on. It is because of this action that the composition of the invention antagonizes the onset of various atherosclerotic diseases.

Consequently, the invention further provides a pharmaceutical composition for inhibiting the expression of adhesion molecules in vascular endothelial cells.

The fact that apM1 inhibits expression of said cell adhesion molecules indicates that the composition of the invention can be indicated for the prophylaxis and therapy of bronchial asthma which is a disease related to type I allergy accompanying eosinophilic infiltration and also known to be a disease associated with an enhanced expression of VCAM-1, for instance.

Furthermore, in view of the fact that said ICAM-1 and ELAM are known to be inflammation-related adhesion molecules, the composition of the invention comprising apM1 as an active ingredient may be indicated as an antiinflammatory agent or a therapeutic drug for rheumatoid arthritis, for instance, by taking advantage of said inhibitory effect on the expression of adhesion molecules.

Furthermore, the composition of the invention is effective in the prevention and treatment of post-angioplasty restenoses, for example in stent PTCA cases. Thus, after an operation for neovascularization against the coronary artery stenosis in angina pectoris or myocardial infarction, the post-ischemic reperfusion and injury of vascular endothelial cells evoke expression of adhesion molecules in vascular endothelial cells and consequent proliferation of smooth muscle cells to induce a restenosis. The composition of the invention inhibits such expression of adhesion molecules and growth of smooth muscle cells to thereby contribute to the prevention of ischemic restenoses after angioplasty.

The method for diagnosis of arteriosclerosis according to the invention utilizes a new marker, that is smooth muscle growth potency (DNA-synthesizing ability of smooth muscle cells). The diagnosis method of the invention is carried out by determining and quantitating the apM1 level in a sample with a specific antibody against apM1.

The production of apM1 for use as the active ingredient of the composition of the invention, preparation of the composition using apM1 as an active ingredient, production of an antibody against apM1, and assay of apM1 are now described in sequence.

The designation of amino acids, peptides, nucleotide sequences, nucleic acids, etc. by abbreviations in this specification is in conformity with the rules of nomenclature recommended by IUPAC-IUB (IUPAC-IUB Communication on Biological Nomenclature, Eur. J. Biochem., 138, 9(1984)), "The Guidelines for Drafting of Specifications Etc. Containing Nucleotide Sequence or Amino Acid Sequence Information" (Edited by the Japanese Patent Office, June, 1998) and the conventions in the relevant field of art.

apM1 can be provided in the form of a recombinant protein by the established genetic engineering techniques [e.g. Science, 224,1431(1984); Biochem. Biophys. Res. Comm.,130, 692(1985); Proc. Natl. Acad. Sci., USA., 80, 5990 (1983)]. In this case, as the apM1 gene, the gene which was previously established by the present inventors can be used [Biochem. Biophys. Res. Commun., 221, 286-289 (1996)].

As an alternative, apM1 can be produced by the conventional method for chemical synthesis in accordance with the information on the amino acid sequence encoded by said gene.

More particularly, the production of apM1 by a genetic engineering technique comprises constructing a recombinant DNA with which the gene coding for the objective protein may be expressed in a host cell, introducing the DNA into the host cell to obtain a transformant and culturing the transformant.

As the host cell mentioned above, cells derived from eucaryotes and prokaryotes can be employed. The eucaryotic cell includes cells of vertebrates and cells of eucaryotic microorganisms. As the cell of a vertebrate, the monkey cell line COS [Cell, 23, 175 (1981)], the Chinese hamster ovarian cell line and the corresponding dihydrofolate reductase-deficient cell line [Proc. Natl. Acad. Sci., USA., 77, 4216 (1980)] and the like are frequently used but these are not exclusive choices.

As the expression vector of a vertebrate origin, a vector having a promoter sequence located upstream of the gene to be expressed, RNA (precursor) splice site, a polyadenylation site and a transcription terminating sequence, among others, can be generally used. Where necessary, the vector may further have a replication origin. As an example of such expression vector, pSV2dhfr harboring an early promoter of SV40 can be mentioned (Mol. Cell. Biol., 1, 854 (1981)).

As the eucaryotic microorganisms, yeasts are generally used and, among them, yeasts of the genus *Saccharomyces* can be used with advantage. As the expression vector derived from a eucaryotic microorganism such as a yeast, pAM82 having a promoter for the acid phosphatase gene [Proc. Natl. Acad. Sci., USA., 80, 1 (1983)], among others, can be utilized.

As the prokaryotic host, *Escherichia coli* and *Bacillus subtilis* are generally used most frequently. When they are used as hosts, it is advantageous to select a plasmid vector which can be replicated in the host microorganism and in order that the objective gene may be expressed in the vector, use an expression plasmid provided with a promoter region and an SD (Shine-Dalgano) sequence upstream of the gene and, further, with an initiation codon (e.g. ATG) required for the start of protein synthesis. As said *Escherichia coli* as the host, *E. coli* K12 is generally used, and as the vector, pBR322 or its modification product is generally used. However, these are not exclusive choices but the various known bacterial strains and vectors can likewise be employed. Examples of the promoter that can be used are tryptophan (trp) promoter, 1pp promoter, lac promoter, and PL/PR promoter.

Introduction of the resulting recombinant DNA into the host cell for transformation can be carried out in the routine manner.

The transformant obtained can be cultivated by the conventional manner, whereby the objective recombinant protein is expressed, produced, and accumulated or secreted intracellularly, extracellularly or on the cell membrane. The medium for the cultivation can suitably be selected from among various media in routine use according to the host cell selected. The cultivation of the transformant can also be carried out under conditions suited to the particular host cell.

Where necessary, the apM1 obtained in the above manner can be isolated and purified by various separation procedures utilizing the physical, chemical and other characteristics thereof [Biochemical Data Book II, 1175-1259, First Edition, 1st impression, Jun. 23, 1980, published by Tokyo Kagaku Dojin, K. K.; Biochemistry, 25 (25), 8274 (1986); Eur. J. Biochem., 163, 313 (1987), etc.]. More particularly, said isolation and purification can be achieved by the conventional reconstitution treatment, treatment with a protein-precipitating (salting-out) agent, centrifugation, osmotic pressure shock method, sonication, ultrafiltration, various types of liquid chromatography such as molecular sieve chromatography (gel filtration), adsorption chromatography, ion-exchange chromatography, affinity chromatography, high-performance liquid chromatography (HPLC), etc., dialysis, and so on, as used either singly or in combination.

Alternatively, the apM1 mentioned above can also be produced by the general method for chemical synthesis based on the amino acid sequence information. The method includes the conventional liquid-phase and solid-phase methods for peptide synthesis. In more detail, each of these methods includes the so-called stepwise elongation technique which comprises condensing component amino acids one after another for chain extension according to the amino acid sequence information, and the fragment condensation technique which comprises synthesizing fragment peptides each consisting of several amino acid residues in advance and coupling them together one after another according to said information.

The condensation reaction for use in the above method of peptide synthesis can also be carried out in the conventional manner. For example, the method which can be used includes the azide method, mixed acid anhydride method, DCC method, activated ester method, redox method, DPPA (diphenylphosphoryl azide) method, DCC+ additive (e.g. 1-hydroxybenzotriazole, N-hydroxysuccinimide, or N-hydroxy-5-norbornene-2,3-dicarboximide) method, and Woodward's method, among others.

The solvent that can be used in those methods can also suitably be selected from among those solvents which are well known to be of use in peptide-forming condensation reactions. As specific examples, N,N-dimethylformamide (DMF), dimethyl sulfoxide (DMSO), hexaphosphoramide, dioxane, tetrahydrofuran (THF), ethyl acetate, etc., inclusive of mixtures thereof, can be mentioned.

In conducting the peptide synthesis reactions, the carboxyl groups of amino acids or peptides which are not to be involved in the respective reactions can be protected generally by esterification, e.g. in the form of a lower alkyl ester, e.g. methyl ester, ethyl ester or tert-butyl ester, or an aralkyl ester, e.g. benzyl ester, p-methoxybenzyl ester or p-nitrobenzyl ester.

Amino acids having a functional group in the side chain, for example the hydroxyl group of a tyrosine residue, may be protected with acetyl, benzyl, benzyloxycarbonyl, tert-butyl or the like, although such protection is not necessarily indispensable.

Moreover, the guanidino group of an arginine residue, for instance, can be protected with a suitable protective group such as nitro, tosyl, p-methoxybenzenesulfonyl, methylene-2-sulfonyl, benzyloxycarbonyl, isobornyloxycarbonyl or adamantyloxycarbonyl.

The reactions for elimination of such protective groups from the protected amino acids or peptides, or from the final protein, can also be carried out by the conventional procedures, for example by the catalytic reduction method or by the method using liquid ammonia/sodium metal, hydrogen fluoride, hydrogen bromide, hydrogen chloride, trifluoroacetic acid, acetic acid, formic acid, or methanesulfonic acid.

The apM1 thus obtained can be purified by the various procedures mentioned hereinbefore, for example the procedures in routine use in peptide chemistry, such as ion exchange chromatography, partition chromatography, gel permeation chromatography, counter-current distribution, and so forth.

The composition of the invention comprises apM1 or a pharmacologically acceptable salt thereof as an active ingredient. The salt includes those with alkali metals, alkaline earth metals and ammonium, such as the sodium, potassium, lithium, calcium, magnesium, barium and ammonium salts. These salts can be produced by the methods well known in the art. The above-mentioned salt further includes acid addition salts which can be prepared by reacting apM1 with a suitable organic or inorganic acid in the per se known manner. Examples of the acid addition salts are hydrochloride, hydrobromide, sulfate, bisulfate, acetate, oxalate, valerate, oleate, laurate, borate, benzoate, lactate, phosphate, p-toluenesulfonate (tosylate), citrate, maleate, fumarate, succinate, tartrate, sulfonate, glycolate, ascorbate, benzenesulfonate, napsylate and like salts.

The composition according to the invention is generally provided and put to use in the form of a pharmaceutical preparation containing a pharmacologically effective amount of said active ingredient together with a suitable pharmaceutical carrier.

The carrier that can be utilized in such a pharmaceutical preparation includes various diluents and/or excipients, such as fillers, volume builders, binders, humectants, disintegrators, surfactants, lubricants, and the like. These carriers are conventionally used according to the desired unit dosage form.

The unit dosage forms of the pharmaceutical preparation can be selected from a broad variety according to the therapeutic objectives. Typical examples include solid forms such as tablets, pills, powders, fine powders, granules and capsules, and liquid forms such as a solution, a suspension, an emulsion, syrup and an elixir. These preparations are classified, by route of administration, into oral preparations, parenteral preparations, transnasal preparations, vaginal preparations, rectal suppositories, sublingual tablets, ointments, and the like, and each can be formulated and molded or otherwise processed by the established pharmaceutical procedure. Furthermore, such pharmaceutical preparations may be supplemented with various additives which can be formulated in ordinary pharmaceutical preparations, such as the stabilizer, antibacterial agent, buffer, isotonizing agent, chelating agent, pH control agent and surfactant, each at a suitable level.

The stabilizer includes human serum albumin and those L-amino acids, carbohydrates and cellulose derivatives which are conventionally used. These can be used each alone or in combination with a surfactant or the like. Particularly, such a combination may contribute to an enhanced stability of the active ingredient.

The L-amino acids are not particularly restricted but include glycine, cysteine, glutamic acid and so on.

The carbohydrates are not particularly restricted but include monosaccharides such as glucose, mannose, galactose and fructose; sugar alcohols such as mannitol, inositol and xylitol; disaccharides such as sucrose, maltose and lactose; and polysaccharides such as dextran, hydroxypropyl-starch, chondroitin sulfate and hyaluronic acid; inclusive of derivatives thereof.

The surfactants are not particularly restricted but ionic and nonionic surfactants can be employed. Examples of the surfactants are polyoxyethylene glycol sorbitan alkyl esters, polyoxyethylene alkyl ethers, sorbitan monoacyl esters, and fatty acid glycerides.

The cellulose derivatives are not particularly restricted but include methylcellulose, ethylcellulose, hdroxyethylcellulose, hydroxypropylcellulose, hydroxypropylmethylcellulose, carboxymethylcellulose sodium and so on.

The carbohydrates can be used at least about 0.0001 mg, preferably within the range of about 0.01-10 mg per 1 µg of the active ingredient. The surfactants can be used at least about 0.00001 mg, preferably within the range of about 0.0001-0.01 mg per 1 µg of the active ingredient. The human serum albumin can be used at least about 0.0001 mg, preferably within the range of about 0.001-0.1 mg per 1 µg of the active ingredient. The amino acids can be used within the range of about 0.001-10 mg per 1 µg of the active ingredient. The cellulose derivatives can be used at least about 0.00001 mg, preferably within the range of about 0.001-0.1 mg per 1 µg of the active ingredient.

The proportion of the active ingredient in the pharmaceutical preparation of the invention can be liberally selected from a broad range. Generally, the active ingredient accounts for the range of about 0.00001-70 weight %, preferably about 0.0001-5 weight % of the final preparation.

The buffer which may be optionally incorporated in the pharmaceutical preparation includes boric acid, phosphoric acid, acetic acid, citric acid, ε-aminocaproic acid, glutamic acid and the corresponding salts (e.g. salts with alkali metals or alkaline earth metals such as the sodium, potassium, calcium and magnesium salts). The isotonizing agent includes sodium chloride, potassium chloride, sugars and glycerine, among others. The chelating agent includes sodium edetate and citric acid.

The pharmaceutical preparation of the invention encompasses not only liquid preparations but also lyophilized preparations for extemporaneous reconstitution as prepared by freeze-drying liquid preparations for extended shelf lives. The lyophilized preparations are to be administered after dissolution in water or a buffer solution inclusive of physiological saline.

In molding the pharmaceutical composition of the invention into the tablet form, there can be used, as the carrier, various excipients such as lactose, sucrose, sodium chloride, glucose, urea, starch, calcium carbonate, kaolin, crystalline cellulose, silicic acid and potassium phosphate; binders such as water, ethanol, propanol, simple syrup, glucose solution, starch solution, gelatin solution, carboxymethyl cellulose, hydroxypropyl cellulose, methyl cellulose and polyvinyl pyrrolidone; disintegrators such as sodium carboxymethyl cellulose, calcium carboxymethyl cellulose, low-substituted hydroxypropyl cellulose, dry starch, sodium alginate, agar powder, laminaran powder, sodium hydrogen carbonate and calcium carbonate; surfactants such as polyoxyethylene sorbitan fatty acid ester, sodium lauryl sulfate and stearyl monoglyceride; disintegration inhibitors such as sucrose, stearin, cacao butter and hydrogenated oil; absorption promoters such as quaternary ammonium base and sodium lauryl sulfate; humectants such as glycerin and starch; adsorbents such as starch, lactose, kaolin, bentonite and colloidal silicic acid; and lubricants such as purified talc, stearic acid salt, boric acid powder and polyethylene glycol.

Furthermore, where necessary, the tablets obtained can be coated with the conventional coating materials to provide sugar-coated tablets, gelatin-coated tablets, enteric tablets, film-coated tablets or double- or multi-layer tablets.

The pills can be prepared using, as the carrier, excipients such as glucose, lactose, starch, cacao butter, hydrogenated vegetable oil, kaolin and talc; binders such as gum arabic powder, gum tragacanth powder, gelatin and ethanol, and disintegrators such as laminaran and agar.

Capsules are generally manufactured by formulating the active ingredient with a carrier or carriers such as those mentioned above by way of example and encapsulating the composition using hard gelatin or soft capsule shells, for instance.

The liquid preparation for oral administration includes solutions, emulsions, suspensions, syrup and elixirs. Each can be prepared using a conventional inert diluent, for example a pharmacologically acceptable vehicle inclusive of water. The liquid preparation may further be supplemented with various auxiliary agents such as a wetting agent, an emulsifier and/or a suspending agent and can be prepared by the established procedure.

The liquid preparation for parenteral administration, for example a sterile aqueous or nonaqueous solution, emulsion or suspension, can be prepared by using a diluent such as water, ethyl alcohol, propylene glycol, polyethylene glycol, ethoxylated isostearyl alcohol, polyoxylated isostearyl alcohol, polyethoxylated sorbitan fatty acid esters and vegetable oils such as olive oil. The liquid preparation may be supplemented with an organic ester which can be injected or infused, such as ethyl oleate. Such preparations may be further supplemented with the solubilizer, buffer, wetting agent, emulsifier, suspending agent, preservative, dispersant and other additives.

Such pharmaceutical preparations can be sterilized by filtration through a bacterial filter, incorporation of a bactericide, irradiation treatment, heat treatment, or the like. Moreover, such pharmaceutical preparations may each be provided in the form of a sterile solid composition, which can be dissolved in sterilized water or a suitable sterilizable medium for extemporaneous sterilization.

Rectal suppositories and vaginal preparations can be prepared by using polyethylene glycol, cacao butter, a higher alcohol, a higher alcohol ester, gelatin or a semi-synthetic glyceride as the carrier or base.

Ointments such as pastes, creams and gels can be prepared by using such a diluent or diluents as white petrolatum, paraffin, glycerin, cellulose derivatives, propylene glycol, polyethylene glycol, silicones, bentonite, and vegetable oils such as olive oil.

Pharmaceutical preparations for transnasal or sublingual administration can be prepared using the well-known standard excipient or excipients in the conventional manner.

Furthermore, where necessary, the pharmaceutical preparation of the invention can be supplemented with coloring agents, preservatives, perfumes, flavors, sweeteners or other pharmaceutical compositions.

The method for administration of said pharmaceutical preparation is not particularly restricted but can be judiciously selected with reference to the dosage form, patient background inclusive of age and sex, severity of illness, and other conditions. For example, the tablets, pills, solutions, suspensions, emulsions, granules and capsules are orally administered. The injections are intravenously administered either alone or in admixture with an ordinary infusion such as glucose and amino acid, and if necessary, administered alone intramuscularly, intradermally, subcutaneously or intraperitoneally. The suppositories are inserted into the rectum, while vaginal preparations are administered into the vagina. Transnasal preparations are administered into the nostrils, sublingual preparations into the oral cavity, and ointments for transdermal absorption.

The amount of the active ingredient to be contained in said pharmaceutical preparation and the dosage are not particularly restricted but each can be judiciously selected from a broad range according to the expected therapeutic effect, method of administration, treatment time, patient factors such as age and sex. The dosage is usually selected so that the blood concentration of the active ingredient will be preferably about 1-200 μg/ml, more preferably about 10-20 μg/ml. This preparation can be administered once or in a few divided doses a day.

Production of a specific antibody against apM1 is now described in detail. The specific antibody against apM1 can be produced as an antiserum (polyclonal antibody) or a monoclonal antibody by utilizing apM1, a fragment thereof or a complex protein containing it as a hapten as an immunogen.

The technology for producing such antibodies are well understood by those skilled in the art. The antibody according to the invention can also be produced in accordance with the known method [e.g. Biochemical Experiments Series: "Methods for Immunobiochemical Research", Japanese Biochemical Society (ed.) (1986)].

More particularly, the monoclonal anti-apM1 antibody can be produced by, for example, a process which comprises constructing a fusion cell (hybridoma) between a plasmocyte (immunocyte) from a mammal immunized with said immunogen and a plasmacytoma cell of mammal origin, selecting a clone producing the desired apM1-recognizing antibody, and cultivating the clone.

The apM1 that can be used as an immunogen in the above procedure is not particularly restricted but may be any of the known recombinant apM1 species prepared by the recombinant DNA technology, a peptide having a partial amino acid sequence thereof, or the corresponding conjugated protein containing a prosthetic group. The apM1 mentioned above is known to be an adipose tissue-specific secretory factor and any protein having the equivalent activity or action, for example GBP 28 (gelatin-binding protein of 28 kDa), can also be used likewise as said immunogen.

The mammal to be immunized with said immunogen in the above procedure is not particularly restricted but is preferably selected from the standpoint of compatibility with the plasmacytoma cell to be used in cell fusion. Generally, the mouse, rat or rabbit is used with advantage.

The immunization of said mammal is carried out by the routine method, for example by injecting said immunogen by the intravenous, intradermal, subcutaneous, or intraperitoneal route. Preferably, the immunogen is administered alone or optionally in combination-with an ordinary adjuvant to a laboratory animal, such as the mouse, several times at 2- to 14-day intervals, in a total dose of about 100-500 μg/mouse. As the immunogen, it is preferable to use splenocytes isolated about 3 days after the last immunization.

As regards the mammalian plasmacytoma cell as the other parent cell to be fused with the immunocyte, any of the various cells already known, for example p3 (p3/×63-Ag8) [Nature, 256, 495-497 (1975)], p3-U1 [Current Topics in Microbiology and Immunology, 81, 1-7 (1978)], NS-1 [Eur. J. Immunol., 6, 511-519 (1976)], MPC-11 [Cell, 8, 405-415 (1976)], SP2/0 [Nature, 276, 269-270 (1978)], FO [J. Immunol. Meth., 35, 1-21 (1980)], ×63.6.5.3. [J. Immunol., 123, 1548-1550 (1979)], S194 [J. Exp. Med., 148, 313-323 (1978)], etc. and myeloma cells such as rat R210 [Nature, 277, 131-133 (1979)], can be employed.

The cell fusion reaction between said immunocyte and plasmacytoma cell can be carried out generally in accordance with the method of Milstein et al. [Methods in Enzymology, Vol. 73, p. 3 (1981)], for instance. More particularly, the above fusion reaction can be conducted in a usual medium in the presence of an ordinary fusion inducer, such as polyethylene glycol (PEG), Sendai virus (HVJ) or the like. To achieve an improved fusion efficiency, the medium may be optionally supplemented with an auxiliary agent such as dimethyl sulfoxide.

The ratio of the immunocyte to the plasmacytoma cell for use is not different from the ratio commonly used in this type of procedure. Thus, for example, the immunocyte is generally used in a proportion of about 1- to 10-fold as large as the amount of the plasmacytoma cell. Examples of the medium useful for the cell fusion are RPMI-1640 and MEM, which are generally used for proliferation of plasmacytoma cells, and other media which are used for cell culture of this kind. It is usually preferable that the serum component such as fetal calf serum (FCS) be omitted from the medium formulations.

Fusion is achieved by a procedure which comprises mixing predetermined amounts of said immunocyte and plasmacytoma cell thoroughly in said medium and adding a solution of PEG, for example a PEG with an average molecular weight of about 1000-6000, which has been prewarmed to about 37° C., to the medium usually in a concentration of about 30-60 w/v %, followed by stirring. Thereafter, serial addition of a suitable medium, centrifugation and removal of the supernatant are repeated until the desired hybridoma has been obtained.

The hybridoma thus produced can be isolated by cultivating it in a usual selection medium, such as HAT (a medium containing hypoxanthine, aminopterin and thymidine). This culture using HAT medium is carried out for a sufficient time to kill the cells (unfused cells etc.) other than the desired hybridoma, usually for several days to a few weeks. The resulting hybridoma is subjected to a search for the clone producing the desired antibody by the usual limiting dilution method, followed by the production of monoclonal antibody.

The search for the desired antibody-producing clone can be carried out by the various methods in routine use for detection of antibodies, such as ELISA [Engvall, E., Meth. Enzymol., 70, 419-439 (1980)], plaque method, spot method, agglutination method, Ouchterlony method and radioimmunoassay (RIA) [Hybridoma Techniques and Monoclonal Antibodies, published by R&D Planning, K.K., pp. 30-53, Mar. 5, 1982]. The immunogen mentioned hereinbefore can be used for the purpose of this search.

The thus-obtained hybridoma producing the desired monoclonal antibody which recognizes apM1 can be subcultured in ordinary media and can also be stored for a long time in liquefied nitrogen.

Harvesting of the desired antibody from the above hybridoma can be effected by the method which comprises cultivating the hybridoma in the routine manner and harvesting the antibody as a culture supernatant or the method which comprises inoculating a compatible mammal with the hybridoma to cause it to multiply and harvesting the antibody as an ascites fluid. The former method is suitable for preparation of the antibody of high purity and the latter method is suitable for mass production of the antibody.

The antibody thus obtained can be purified by the conventional procedure such as precipitation, gel filtration, affinity chromatography, and so forth. In this manner, the desired anti-apM1 monoclonal antibody which specifically binds apM1 can be obtained.

The invention further provides a technique for the assay of apM1 in a sample and an associated method for diagnosis of arteriosclerosis.

The diagnosis of arteriosclerosis according to the invention comprises determining the amount of apM1 in a patient's blood or urine sample with the anti-apM1 antibody by a liquid-phase or solid-phase immunoassay technique and comparing the measured value with the corresponding value in patients with arteriosclerosis and the corresponding value in healthy persons to see whether the apM1 level in the sample is higher or lower than the level in healthy persons.

The preferred immunoassay method is ELISA by the sandwich technique.

The above method is now described in detail. Its principle is based on the enzyme antibody method. Thus, this method typically comprises sowing an anti-human apM1 monoclonal antibody (the first antibody) on a 96-well plate and, to prevent nonspecific adsorption, carrying out blocking (immobilization). To this monoclonal antibody-immobilized plate, the human apM1 standard solution or the test sample is added and reacted (the first reaction). After the plate is washed, the anti-human apM1 antibody (the second antibody) is added and reacted (the second reaction). The plate is washed and the HRP-labeled anti-rabbit IgG antibody (the third antibody) is added and reacted (the third reaction). After the plate is washed, the substrate is added and the enzymatic reaction is carried out (the fourth reaction). Then, the activity is read as the absorbance at the wavelength of 492 nm.

In the above procedure, it is also possible to use the polyclonal antibody as the first antibody and the monoclonal antibody as the second antibody.

In the above method, the higher the concentration of apM1 in the standard solution or test sample used is, the higher is the enzyme activity (absorbance) detected. By constructing a standard curve (calibration curve) by plotting the absorbance values of standard solutions and comparing the absorbance of the test sample with the curve, the amount of apM1 in the test sample can be expediently found to diagnose whether the patient has arteriosclerosis or not.

Furthermore, the above diagnosis of arteriosclerosis according to this invention can be carried out more expediently by means of a kit and this invention further provides such a kit.

The kit of the invention and the method of detecting the amount of apM1 in a test sample are now described in detail.

In the assay procedure using the kit of the invention, the test sample is preferably a urine sample or a blood sample (particularly a serum or plasma sample from fasted blood), and such a sample can be obtained and prepared from the test subject in the routine manner.

The kit according to the invention comprises an anti-apM1 monoclonal or polyclonal antibody (anti-apM1 antibody) as an essential component, preferably a combination thereof with the anti-apM1 polyclonal antibody or monoclonal antibody, respectively, as the case may be, or a combination of said monoclonal antibodies.

The monoclonal antibody mentioned above is preferably used as immobilized by coupling it to a carrier on a plate in advance. As an alternative, said antibody can be directly used in an affinity gel form or used as the gel prepared in a vessel or test tube which can be shaken and centrifuged and lends itself to extraction of the non-affinity gel-bound fraction.

It is also preferable to equilibrate said antibody-immobilized plate or gel in advance with a suitable buffer solution, for example 0.01M Tris-HCl buffer (pH 7.4)+0.15M NaCl. Furthermore, said antibody-immobilized plate or gel may be supplemented with a usual preservative such as sodium azide.

More preferably, as an additional component of the kit of the invention, a labeled anti-human apM1 polyclonal antibody is supplied as the second antibody for ELISA. Where necessary, the kit of the invention may further comprise a stabilizer such as saccharose or bovine serum protein and/or a preservative. The preservative is selected from among substances which do not affect the test result with the kit and includes a diluted solution of sodium azide as a representative example.

Moreover, the kit of the invention may optionally comprise a water-soluble or -miscible substance such as glycerin, alcohol, glycol, glycoether or the like and, for degreasing purposes, a mixed organic solvent such as ethanol-diethyl ether, methanol-diethyl ether, or chloroform-methanol.

BEST MODE FOR CARRYING OUT THE INVENTION

The following examples illustrate the invention in further detail and should not be limitative of the scope of the invention.

EXAMPLE 1

Production of a recombinant apM1

(1) Expression of apM1 in *Escherichia coli*

1) apM1 PCR

The nucleotide sequence of the apM1 gene and the amino acid sequence encoded thereby have been deposited with the GenBank under the accession number of D45371. The coding region (CDS) is shown as the sequence from 27th to 761st of the nucleotide sequence. Its deduced amino acid sequence is shown in SEQ ID NO:1. In this sequence, the 1st to 14th residues constitute a signal peptide and the 15th to 244th residues represent the mature apM1.

Figure 1:
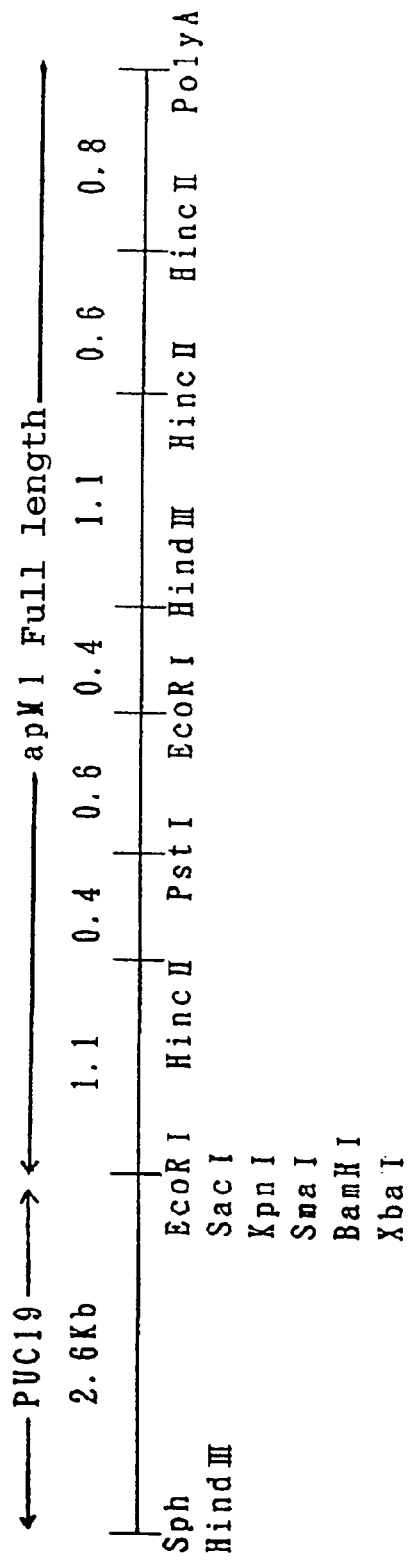
FIG. 1 shows a restriction enzyme map of a plasmid containing the nucleotide sequence of the apM1 gene.
Figure 2:
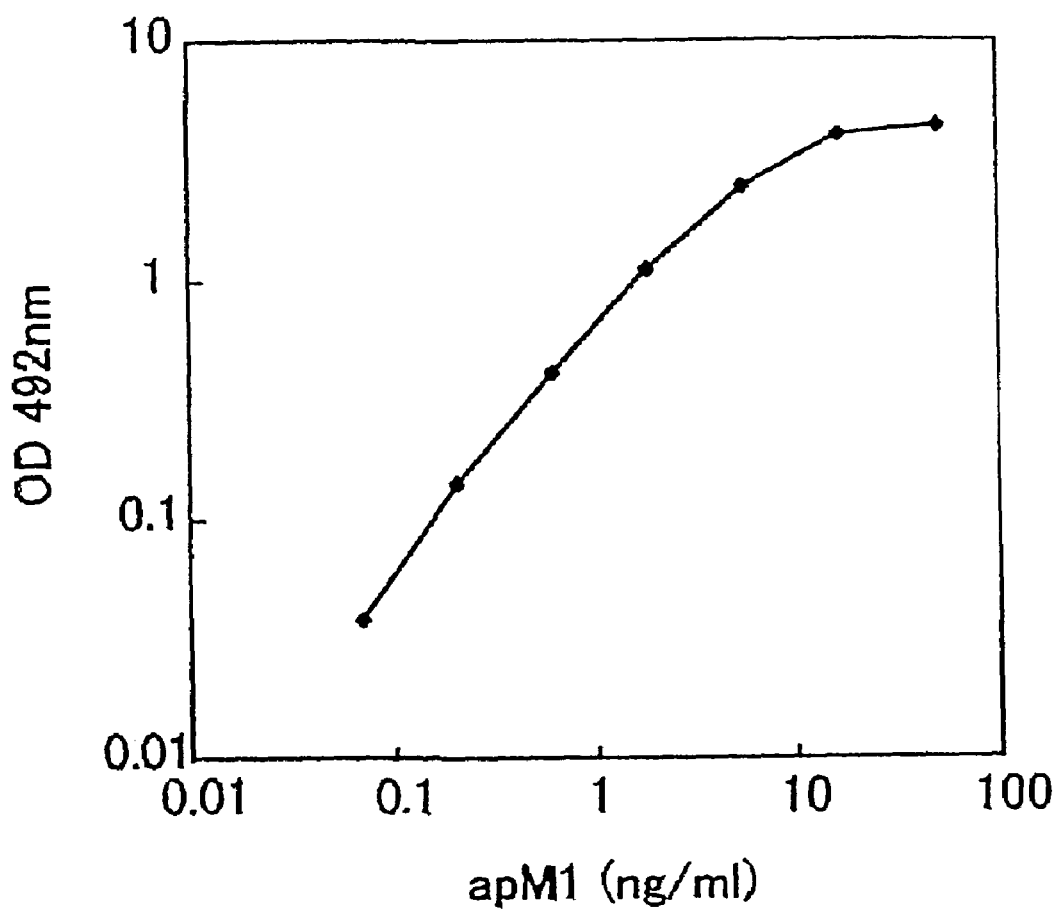
FIG. 2 shows a standard curve constructed by using a recombinant apM1.

The apM1 gene was amplified by PCR using the plasmid donated by Dr. Funahashi, the Second Department of Internal medicine, Osaka University School of Medicine as a template. The restriction enzyme map of the plasmid containing the nucleotide sequence of the apM1 gene is shown in FIG. 1.

Designing so that the 693 bp sequence from 69th to 761st of the nucleotide sequence of the apM1 would be amplified with an NdeI site at the 5'-end and a BamHI site at the 3'-end, PCR primers were produced using an automatic DNA synthesizer. The PCR primer sequences are shown in SEQ ID NO:3 (forward) and NO:4 (reverse).

2) Subcloning of the apM1 Gene

The PCR product obtained in the above step 1) was subcloned into pT7 Blue T-Vector (Novagen) and it was confirmed that there was no mutation in its nucleotide sequence (pT7-apM1).

3) Construction of an Expression Vector

The expression vector pET3c (Novagen) was digested with NdeI and BamHI to recover a fragment of approximately 4600 bp. On the other hand, the pT7-apM1 obtained in the above step 1) was digested with NdeI and BamHI to recover a fragment of approximately 700 bp. These fragments were ligated and the expression vector thus obtained was named pET3c-apM1.

4) Expression in *Escherichia coli*

The host *E. coli* strain BL21(DE3)pLysS was transformed with the pET3c-apM1 constructed in the above step 3) and cultured in 2×T.Y.Amp. (tryptone 16 g, yeast extract 10 g, and NaCl 5 g). When the organism had entered into the logarithmic growth phase, IPTG (isopropyl β-D-thiogalactopyranoside) was added for inducing the production of a recombinant apM1. The *E. coli* cells before and after this IPTG induction and the inclusion body (the insoluble fraction of *E. coli*) after said IPTG induction were sampled and subjected to SDS-PAGE and Western blotting to confirm the expression of apM1.

5) Results and Discussion

The expression product in *E. coli*, obtained in the above manner, was a 230-residue protein corresponding to the $^{15}$Gly to $^{244}$Asn, exclusive of the signal sequence, of the amino acid sequence of apM1, with the addition of Met derived from the initiation codon at the N-terminus. This amino acid sequence is shown in SEQ ID NO:2.

The *E. coli* obtained by the above procedure was analyzed by SDS-PAGE. As a result, an approximately 30 kD band could be confirmed in the *E. coli* cell and inclusion body after IPTG induction.

Then, Western blotting was performed using two kinds of antibodies [polyclonal antibodies (synthetic peptides)]. Both antibodies reacted with said approximately 30 kD band, whereas no reaction was detected at all with the host *E. coli*.

The above approximately 30 kD band was excised to investigate the sequence of its 10 amino acid residues at N-terminal. The sequence was the same as the expected sequence, with the deletion of the N-terminal Met having been found in a minor population.

It became clear from the above results that the recombinant apM1 had been expressed as an approximately 30 kD protein. Most of the recombinant apM1 expressed had been intracellularly accumulated as an inclusion body.

(2) Purification of the Recombinant apM1 from *E. coli*

Purification of the recombinant apM1 from *E. coli* was carried out by the following 5-step procedure.

1) Culture of *E. coli*

The *E. coli* BL21(DE3)pLysS (Novagen) transformed with the expression vector pET3c-apM1 was precultured in 2×T.Y.Amp.Cm. (tryptone 16 g, yeast extract 10 g, chloramphenicol 25 μg/ml, and NaCl 5 g) (37° C., shake culture). On the following day, the culture was diluted with 100 volumes of 2×T.Y.Amp. and further incubated. After 2-3 hours of incubation when the OD550 of the culture fluid had become 0.3-0.5, IPTG was added at a final concentration of 0.4 mM for inducing the production of recombinant apM1. About 3-5 hours after addition of IPTG, the culture fluid was centrifuged (5000 rpm, 20 min., 4° C.) and the *E. coli* pellet thus obtained was stored frozen.

2) Preparation of an Inclusion Body from *E. coli*

The *E. coli* pellet was suspended in 50 mM Tris-HCl (pH 8.0) and treated with lysozyme at 37° C. for 1 hour. Then, Triton X-100 (Katayama Kagaku) was added at a final concentration of 0.2%. This solution was sonicated (Branson Sonifier, output control 5, 30 sec.) and centrifuged (12000 rpm, 30 min, 4° C.) and the pellet was recovered. This pellet was suspended in 25 ml of 0.2% Triton X-100-supplemented 50 mM Tris-HCl (pH 8.0) and the suspension was sonicated (under the same conditions as above).

The resulting solution was centrifuged and the pellet was washed by the same procedure as above. The pellet thus obtained was taken as the inclusion body.

3) Refolding of the Inclusion Body

The inclusion body was solubilized with a small quantity of 7 M guanidine HCl, 100 mM Tris-HCl (pH 8.0) and 1% 2ME. This solution was dropped into 200-fold volume of 2 M urea, 20 mM Tris-HCl (pH 8.0) for dilution and allowed to stand at 4° C. for 3 nights.

4) Concentration of the Refolded Solution

The solution after the above refolding was centrifuged (9000 rpm, 30 min, 4° C.) and the supernatant was concentrated to about 1/100 by ultrafiltration using an Amicon YM-10 membrane. This concentrate was dialyzed against 20 mM Tris-HCl (pH 8.0) and the dialysate was filtered through a 0.45 μm filter.

5) DEAE-5PW Anion-Exchange HPLC

The sample obtained in the above step 4) was fractionally purified by anion-exchange high performance liquid chromatography (HPLC) with DEAE-5PW (Tosoh Corporation). As the starting buffer, 20 mM Tris-HCl (pH 7.2) was used, and elution was carried out on a NaCl gradient (0→1M NaCl/60 ml) under absorbance monitoring at 280 nm. The eluate was collected in 1 ml fractions and each fraction was analyzed by SDS-PAGE.

6) Results and Discussion

Because the recombinant apM1 had been expressed as an inclusion body in *E. coli*, its purification was carried out by solubilization and refolding of the inclusion body. As a result, the recombinant apM1 was solubilized and separated on the anion-exchange column. The peak fractions (fraction Nos. 30-37) were pooled and analyzed by SDS-PAGE. As a result, an approximately 30 kD band was observed. In this analysis, a faint smear band was detected on the background but as most of the protein was considered to be the recombinant apM1. This approximately 30 kD band (recombinant apM1) was used as the antigen in the subsequent immunization of rabbits and mice.

(3) Preparation of Anti-apM1 Polyclonal and Monoclonal Antibodies

1) Preparation of the Polyclonal Antibody

The recombinant apM, 100 μg/body, was mixed with complete adjuvant in a 1:1 ratio and 5 rabbits were immunized with the mixture 8 times at 2-week intervals to obtain an anti-apM1 polyclonal antibody (Identification codes: OCT9101-OCT9105).

2) Preparation of the Monoclonal Antibody

The recombinant apM1, 20 μg/body, was mixed with complete adjuvant in a 1:1 ratio and mice were immunized with the mixture 3 times at 2-week intervals. Then, the final immunization was carried out without the adjuvant 3 days before cell fusion. Cell fusion between the mouse spleen cell and myeloma cell was carried out by the PEG method and the hybridoma was selected in HAT medium.

Screening for an apM1 antibody-producing cell line was carried out by ELISA using the antigen (recombinant apM1)-coated immunoplate, and the hybridoma was cloned by the limiting dilution method.

In the above manner, 11 anti-apM1 antibody producing hybridoma lines named KOCO9101-KOCO9111 were obtained. One hybridoma, among them, was deposited with the National Institute of Bioscience and Human Technology, the Ministry of International Trade and Industry, Japan (NIBH, Higashi 1-1-3, Tsukuba-shi, Ibaraki, Japan) as of Jun. 8, 1998 (original deposit date) (the identification code assigned by the depositor: KOC09108) and the demand for conversion to the deposit under Budapest Treaty was filed as of Oct. 7, 1998. The accession number of the final deposit is FERM BP-6542.

The hybridomas as single clones were respectively administered intraperitoneally to mice treated with pristane in advance and the ascites fluid was harvested (Identification codes: ANOC9101-9111).

3) Purification of Antibodies

The rabbit antiserum (polyclonal antibody) and mouse ascites fluid (monoclonal antibody) were respectively purified using a protein A column.

4) Expression of apM1 in Animal Cells

The cDNA of the apM1 was excised with EcoRI and inserted into the EcoRI site of the expression vector pCIneo (Promega Corp.). The COS-1 cell (ATCC CRL1650) was transfected with the above pCIneo-apM1 using LlipofectAMINE, GIBCO BRL, and the culture supernatant and the cells were respectively harvested after 72 hours.

5) Western Blotting of apM1

First, the adipose tissue extract, COS-1 cells, COS-1 cell culture supernatant, healthy human plasma, and recombinant apM1 were subjected to 2 ME(+) SDS-PAGE and transferred to a nitrocellulose membrane.

This membrane was reacted with the anti-apM1 monoclonal antibody (ANOC9104) and, then, with the HRP-labeled antibody, and detection was carried out with ECL (Western blot detecting reagent, Amersham).

As a result, an approximately 35 kD band was detected for the adipose tissue extract, pCIneo-apM1/COS-1 cell, and healthy human plasma but was not observed for pCIneo/COS-1 cell or pCIneo/COS-1 cell culture supernatant.

With the culture supernatant of pCIneo-apM1/COS-1 cells, a 35 kD band could be confirmed although it was too weak in intensity to be readily discernible.

EXAMPLE 2

Determination of apM1 in Samples

1) Western Blotting of apM1

Healthy human plasma was diluted 1:10 with PBS and 5 µl of the dilution was subjected to 2ME(+), (−)SDS-PAGE and transferred to a nitrocellulose filter. After blocking, the filter was reacted with a 1000-fold dilution of the anti-apM1 polyclonal antibody (OCT9101-9105) or 5 µg/ml of the anti-apM1 monoclonal antibody (ANOC9101-1) and further with HRP-labeled anti-rabbit IgG antibody or HRP-labeled anti-mouse IgG antibody, and detection was carried out with ECL.

As a result, with all the polyclonal antibodies, an apM1 band of approximately 35 kD in the case of 2ME(+) and that of approximately 70 kD in the case of 2ME(−) could be confirmed. Among the monoclonal antibodies, ANOC9104 and ANOC9108 reacted intensely with the apM1 band. The above results suggested that as the monoclonal antibody for use in ELISA, ANOC9104 and ANOC9108 are suitable.

2) Construction of the apM1 ELISA System

The anti-apM1 monoclonal antibody (ANOC9108) was coated on an immunoplate and, after each well was blocked, the apM1 standard and sample were added and incubated. After each well was washed, a dilution of anti-apM1 polyclonal antibody (OCT9104) was added and incubated. After each well of the plate was washed, a dilution of HRP-labeled anti-rabbit IgG antibody was added and incubated. After each well was washed, OPD was added to each well for staining and the absorbance at 492 nm was measured. As the apM1 standard, the recombinant apM1 expressed in E. coli, purified and quantitated for protein by a protein assay using BSA as reference was used.

As a result, the detection range with the above combination of ANOC9108 and OCT9104 was 0.1 ng/ml -20 ng/ml.

3) Gel Filtration and Western Blotting of Healthy Human Plasma

When healthy human plasma was measured by the above apM1 ELISA, the concentration expected from the result of Western blotting analysis could not be obtained. Therefore, the healthy human plasma was subjected to Superose 12 (Pharmacia) gel-filtration and each fraction was subjected to SDS-PAGE and analyzed by Western blotting with ANOC9104. The molecular weight markers were also subjected to gel filtration under the same conditions and their positions were compared with the elution position of apM1.

As a result, apM1 was found to have been broadly eluted in the fractions corresponding to not less than 290 KD in molecular mass. The above findings suggested that apM1 in blood is associated with the other plasma components to form large molecules not less than 290 kD in molecular mass so that the antibody recognition site is masked. With the thought, therefore, that if the plasma be treated with an SDS-containing buffer, the antibody might be enabled to react with apM1, the following study was undertaken.

4) Treatment of a Plasma Sample

The plasma was boiled in an SDS-containing buffer and the conditions of treatment (boiling time, mixing ratio of plasma to SDS buffer) were studied. As to boiling time, the healthy human plasma was diluted 10-fold with SDS buffer and boiled for 10 sec., 30 sec., 1 min., 3 min., 5 min. or 10 min. and after final dilution to 5000-fold from the original plasma, the assay of apM1 was carried out. As regards the mixing ratio of plasma to SDS buffer, a 2, 3, 5, 10 or 20-fold dilution of healthy human plasma in SDS buffer was boiled for 5 minutes and, after final dilution to 10000-fold, the assay of apM1 was carried out.

As a result, apM1 could be detected at levels of the same order as the results of Western blotting of healthy human plasma. Comparison of the above different conditions of treatment suggested that it was appropriate to dilute plasma 10-fold in SDS buffer and boil the dilution for 5 minutes.

5) Dilution of the Plasma Sample

In view of the finding that the detection range of apM1 ELISA is 70 pg/ml-20 ng/ml and that the blood apM1 concentration is of the µg order, it was considered that serum (plasma) must be diluted prior to assay. Therefore, in order to determine the proper dilution factor, the SDS-treated plasma was serially diluted and apM1 in each dilution was assayed. Thus, healthy human serum was treated with SDS and, then, diluted 200-10×$10^4$-fold serially and apM1 was assayed.

As a result, within the measurement range of this ELISA, apM1 was detected in proportion to dilution factor, and in consideration of absorbance, among other conditions, it was considered appropriate to perform assays at an about 5000-fold final dilution.

6) Study of Blood Sampling Conditions

Sampling of blood from healthy subjects was carried out under various conditions: serum, heparin and EDTA, and the differences in apM1 titer according to differences in blood sampling conditions were investigated. Thus, blood sampling was carried out in 10 healthy subjects and each serum (plasma) sample was treated with SDS and apM1 was assayed in a final 5000-fold dilution.

As a result, blood apM1 levels in the 10 healthy subjects showed substantially no difference due to the difference in blood sampling method.

7) Study of Sample Storage Conditions

The conditions of storage of samples for apM1 assays were studied with plasma and SDS-treated plasma samples. Regarding plasma storage conditions, samples left standing at 4° C., room temperature, or 37° C. for 1, 2, 3 and 6 days, respectively, were treated with SDS and, to investigate the influence of the freeze-thaw procedure on plasma, samples subjected to 1, 2, 4 and 8 freeze-thaw cycles, respectively, were treated with SDS, and apM1 was assayed in final 5000-fold dilutions. As to SDS-treated samples, the plasma was diluted 10-fold with SDS buffer, boiled for 5 minutes, diluted 10-fold, and subjected to the same experiment as above.

As a result, under the above conditions, little influence was noted on the measured values of apM1. While the influence of the freeze-thaw procedure was also investigated using plasma and SDS-treated plasma samples, little influence was observed.

8) Study of Diurnal Variation and Circadian Variation

The diurnal and circadian variations in the measured values of apM1 in the sera (plasmas) of healthy subjects were studied. As regards the diurnal variation, the same sample was assayed 8 times and CV was calculated. As to the circadian variation, the same sample was assayed 4 times on different days and CV was calculated.

As a result, the CV of diurnal variation was within 5% and the CV of circadian variation was within 10%.

9) Specificity Study

Swine, bovine, equine, goat, rat and mouse sera were subjected to apM1 ELISA and the specificity of the assay system was studied. The serum from each animal species was treated with SDS buffer and apM1 was assayed in a final series of 100-8100-fold dilutions.

As a result, whereas a cross sensitivity of about 10% was found between bovine and equine sera, substantially no cross sensitivity was observed among other animal species.

EXAMPLE 3

The Smooth Muscle Growth Inhibitory Effect of apM1

A plastic plate was sown with human arterial smooth muscle cells (Clontech) at a concentration of $1\times10^4/cm^2$ and allowed to stand overnight in DMEM (Gibco) supplemented with 10% FBS (Gibco), 100 IU/ml penicillin and 100 µg/ml streptomycin and, then, incubated in 5% $CO_2$+95% air at 37° C.

The DNA synthesis into the human arterial smooth muscle cells was quantitated according to [methyl $^3$H]-thymidine uptake (4 replicates).

Thus, the cells sown on a 96-well plate were treated with 10 µg/ml of apM1 and/or, as control, 10 ng/ml of HB-EGF (recombinant human heparin-binding EGF-like growth factor, R&D Systems) in 2% FBS-DMEM for 24 hours. Then, [methyl $^3$H]-thymidine was added, 1 µCi/well, over 5 hours. The cells were then treated with trypsin and, using an automatic cell harvester, taken out onto a glass fiber filter. Then, the amount of [methyl $^3$H]-thymidine uptake was directly measured with a β-counter.

Figure 3:
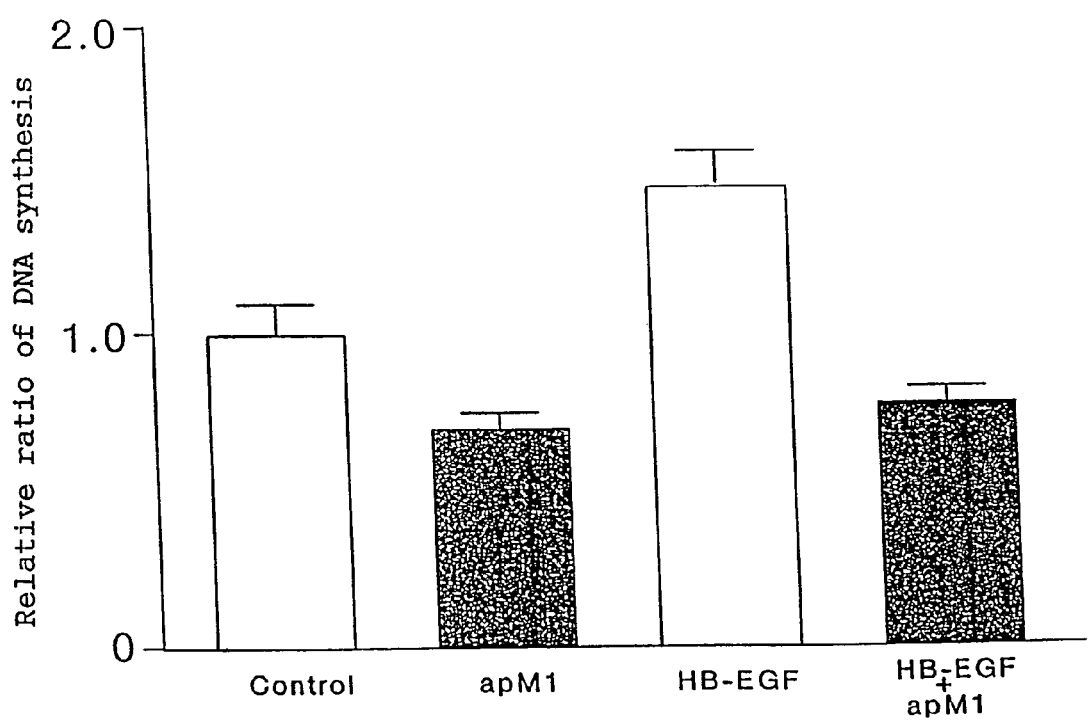
FIG. 3 is a graph showing the smooth muscle antagonizing effect of apM1 as measured in accordance with Example 3.

The results are presented in FIG. 3. This bar graph was constructed by plotting the relative ratio of DNA synthesis on the ordinate against control (no test drug added), addition of apM1 (this invention), addition of HB-EGF (control), and addition of apM1+HB-EGF (this invention) on the abscissa.

It is apparent from the graph that apM1 antagonizes the DNA synthesis of human smooth muscle cells (growth of smooth muscle). Thus, by the addition of apM1, the control DNA synthesis can be significantly ($p<0.001$) inhibited and even the DNA synthesis augmented by HB-EGF can also be significantly ($p<0.001$) inhibited.

These results indicate that apM1 is an effective smooth muscle growth inhibitor.

EXAMPLE 4

Determination of Blood apM1 Levels in Patients with Coronary Artery Disease

In 24 male and 10 female patients verified to have a stenosis of not less than 75% by coronary angiography (indicated as CAD(+)) and 66 male and 39 female patients with a stenosis of less than 75% (indicated as CAD(−)), the blood was collected and the plasma apM1 concentration was determined by the method of the invention as described in Example 2.

At the same time, a CT scan was taken at the umbilical level of each patient and the visceral fat area (VFA, $cm^2$) was calculated from CT findings.

Figure 4:
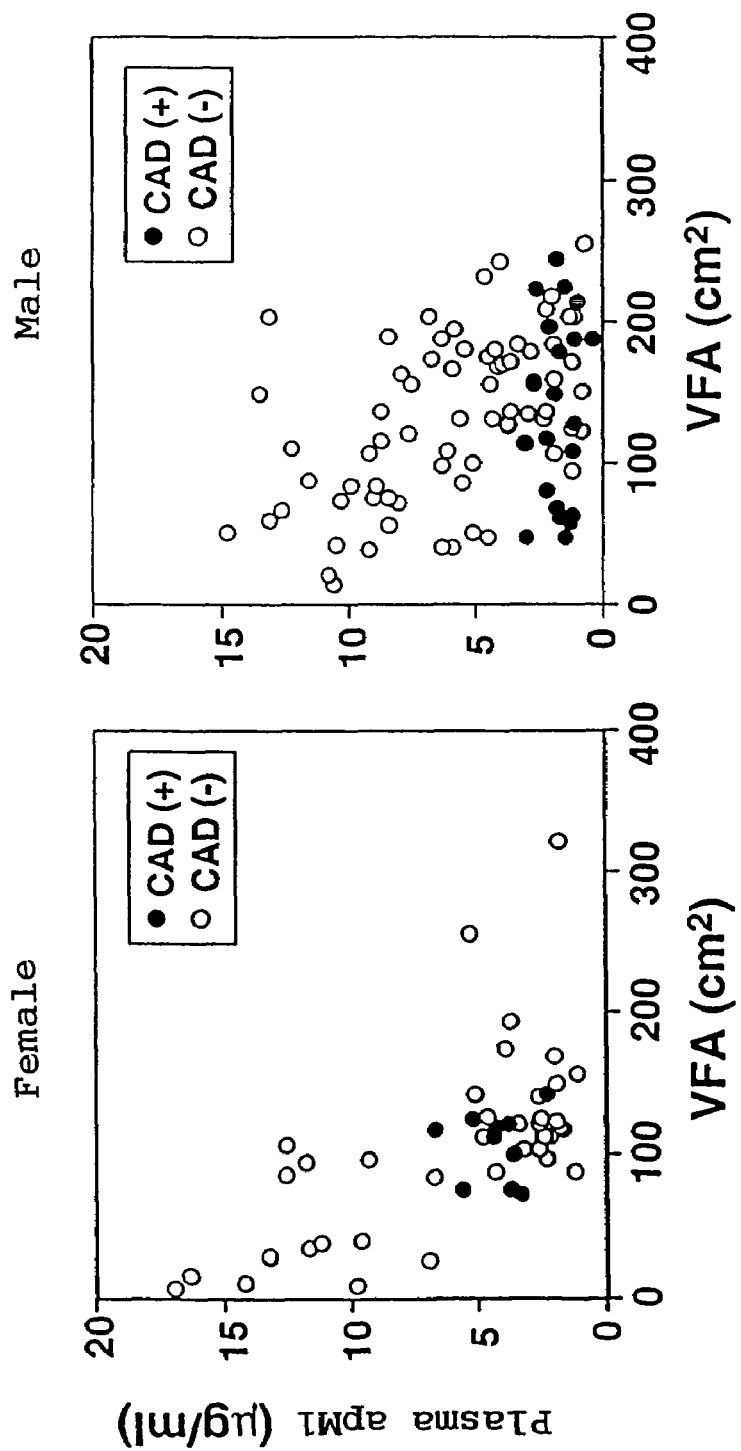
FIG. 4 show diagrammatically the blood apM1 levels in patients with coronary artery disease and healthy subjects as determined in accordance with Example 4.

With the plasma apM1 level (µg/ml) being plotted on the ordinate and VFA on the abscissa, the correlation between the measured value and calculated value was analyzed by the unpaired t-test for the values other than CAD(+) and CAD(+). The results are presented in FIG. 4.

It is apparent from the graph that the apM1 levels in the patients with coronary artery disease [CAD(+) group] were invariably low regardless of the magnitude of visceral fat area (VFA), indicating that apM1 is effective in diagnosing an advanced coronary artery stenosis.

It was also found that apM1 is an important marker of the onset and progression of arteriosclerosis, suggesting its usefulness in the therapy of the disease.

EXAMPLE 5

The Inhibitory Effect of apM1 on the Onset of Arteriosclerosis

Human aortic vascular endothelial cells (HAEC; purchased from Clontech) sown on a 96-well plate were cultured (5% $CO_2$, 37° C.) in the vascular endothelial cell culture medium. Using Becton Dickinson's "Biocoat" (trade name), culture was continued until the growth had become confluent, after which time the medium was changed to TCM 199 [Tissue culture medium 199; Osaka University Microbial Research-Nakalai Tesque]+0.5% FCS (fetal calf serum; Japan Biomaterials)+3% BSA (bovine serum albumin; Sigma).

Then, the recombinant apM1 obtained in Example 1 was added in varying amounts, i.e. 1, 5, 10, 25 and 50 μg/ml, and the system was further incubated for 18 hours. Thereafter, human recombinant TNF-α (tumor necrosis factor-α, R & D; 10 U/ml) was added and the system was further incubated for 6 hours (the apM1-added experimental group).

As a control, the group without addition of said recombinant apM1 (TNF-α stimulation only) was provided.

Using the cell-ELISA method (Takami, S., et al., Circulation, 97 (8), 721-728 (1998)), it was analyzed whether apM1 would suppress the expression of adhesion molecule proteins, namely VCAM-1 (vascular cell adhesion molecule-1), ELAM (endothelial leukocyte adhesion molecule) and ICAM-1 (intercellular adhesion molecule-1), on the HAEC surface by the above TNF-α stimulation. As the anti-ICAM-1 antibody, DAKO's 6.5B5 was used.

The apM1-added group was compared with the apM1-free group and the difference was tested for statistical significance by Student's test.

Figure 5:
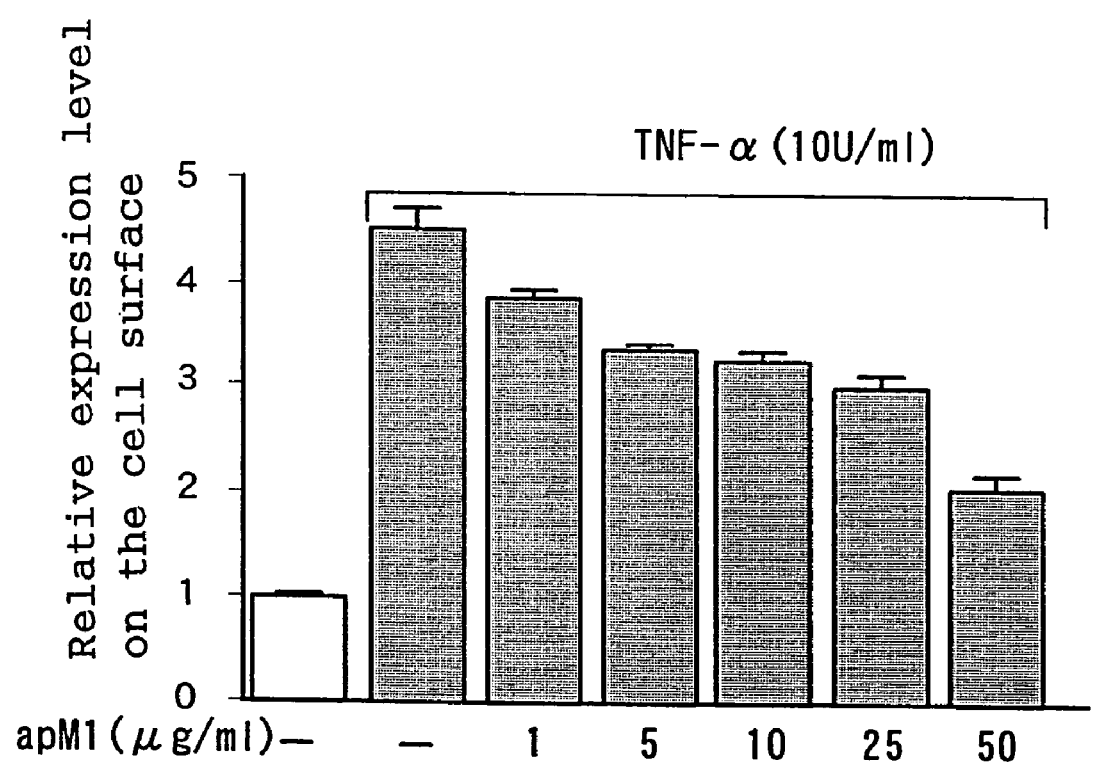
FIG. 5 is a graph showing the concentration-dependent inhibitory effect of apM1 on the expression of an adhesion molecule on the cell surface as determined in accordance with Example 5.

The results for VCAM-1 are presented in FIG. 5.

In FIG. 5, the abscissa represents the level of addition of apM1 (μg/ml; — indicates no addition) while the ordinate represents the relative expression level of the adhesion molecule protein (VCAM-1) in each experimental group or control group, with the expression level of VCAM-1 on the cell surface of HAEC in the absence of TNF-α stimulation being taken as unity (1).

The following can be deduced from FIG. 5. Thus, beginning at the concentration of 1 μg/ml, apM1 inhibited the TNF-α-augmented expression of the adhesion molecule VCAM-1 in HAEC significantly ($p<0.05$) and dose-dependently.

It was also found that the expression of the other major adhesion molecules ELAMI and CAM-1 was similarly inhibited by apM1.

It has been reported that injuries to vascular endothelial cells and the resultant monocyte adhesion are cardinal factors in the pathogenesis of arteriosclerosis [Ross, R., Nature, 362 (6423), 801-804 (1993)]. The finding that apM1 inhibited expression of the adhesion molecules decisive of the onset of arteriosclerosis (VCAM-1, ELAM, ICAM-1, etc.) indicates that apM1 acts in an inhibitory way on the onset of arteriosclerosis, thus being effective as a prophylactic agent for arteriosclerosis.

INDUSTRIAL APPLICABILITY

The invention provides a smooth muscle growth inhibitory composition and a composition for inhibiting the expression of adhesion molecules in vascular endothelial cells, both of which comprise apM1 as an active ingredient. These compositions of the invention are useful in the pharmaceutical field. Furthermore, the invention provides a method for assay of apM1 which comprises using an antibody specific to apM1 and by which a novel method for diagnosis of arteriosclerosis can be established.

---

The invention claimed is:

1. A pharmaceutical composition comprising a pharmacologically effective amount of human adipose tissue-specific secretory factor apM1, or a pharmacologically acceptable salt thereof, in combination with a pharmaceutically acceptable carrier,
wherein said human adipose tissue-specific secretory factor apM1 consists of the amino acid sequence of SEQ ID NO:2.

2. The pharmaceutical composition of claim 1, wherein said pharmacologically effective amount is an amount effective to inhibit the growth of human smooth muscle cells.

3. The pharmaceutical composition of claim 1, wherein said pharmacologically effective amount is an amount effective to inhibit the TNFα augmented expression of VCAM-1 on human vascular endothelial cells.

4. The pharmaceutical composition of claim 3, wherein said pharmacologically effective amount is an amount effective to inhibit the TNFα augmented expression of ELAM and ICAM-I on human vascular endothelial cells.

5. The pharmaceutical composition of claim 1, wherein said pharmaceutically acceptable carrier includes one or more members selected from the group consisting of a filler, a volume builder, a binder, a humectant, a disintegrator, a surfactant, and a lubricant.

6. The pharmaceutical composition of claim 1, wherein said pharmaceutically acceptable carrier includes one or more members selected from the group consisting of a stabilizer, an antibacterial agent, a buffer, an isotonizing agent, a chelating agent, and a pH control agent.

7. The pharmaceutical composition of claim 6, wherein said stabilizer is one or more of human serum albumin, L-amino acid, and a carbohydrate.

8. A method of manufacturing a pharmaceutical composition comprising adding a human adipose tissue-specific secretory factor apM1 consisting of the amino acid sequence of SEQ ID NO: 2 or a pharmaceutically acceptable salt thereof, to a pharmaceutically acceptable carrier.

* * * * *

SEQUENCE LISTING

<160> NUMBER OF SEQ ID NOS: 4

<210> SEQ ID NO 1
<211> LENGTH: 244
<212> TYPE: PRT
<213> ORGANISM: Abdominal fat tissue from myoma uteri

<400> SEQUENCE: 1

```
Met Leu Leu Leu Gly Ala Val Leu Leu Leu Ala Leu Pro Gly His
 1               5                  10                  15

Asp Gln Glu Thr Thr Thr Gln Gly Pro Gly Val Leu Leu Pro Leu Pro
             20                  25                  30

Lys Gly Ala Cys Thr Gly Trp Met Ala Gly Ile Pro Gly His Pro Gly
         35                  40                  45

His Asn Gly Ala Pro Gly Arg Asp Gly Arg Asp Gly Thr Pro Gly Glu
     50                  55                  60

Lys Gly Glu Lys Gly Asp Pro Gly Leu Ile Gly Pro Lys Gly Asp Ile
 65                  70                  75                  80

Gly Glu Thr Gly Val Pro Gly Ala Glu Gly Pro Arg Gly Phe Pro Gly
                 85                  90                  95

Ile Gln Gly Arg Lys Gly Glu Pro Gly Glu Gly Ala Tyr Val Tyr Arg
            100                 105                 110

Ser Ala Phe Ser Val Gly Leu Glu Thr Tyr Val Thr Ile Pro Asn Met
        115                 120                 125

Pro Ile Arg Phe Thr Lys Ile Phe Tyr Asn Gln Gln Asn His Tyr Asp
    130                 135                 140

Gly Ser Thr Gly Lys Phe His Cys Asn Ile Pro Gly Leu Tyr Tyr Phe
```

```
              145                 150                 155                 160
Ala Tyr His Ile Thr Val Tyr Met Lys Asp Val Lys Val Ser Leu Phe
                    165                 170                 175

Lys Lys Asp Lys Ala Met Leu Phe Thr Tyr Asp Gln Tyr Gln Glu Asn
            180                 185                 190

Asn Val Asp Gln Ala Ser Gly Ser Val Leu Leu His Leu Glu Val Gly
                195                 200                 205

Asp Gln Val Trp Leu Gln Val Tyr Gly Glu Gly Arg Asn Gly Leu
        210                 215                 220

Tyr Ala Asp Asn Asp Asn Asp Ser Thr Phe Thr Gly Phe Leu Leu Tyr
225                 230                 235                 240

His Asp Thr Asn

<210> SEQ ID NO 2
<211> LENGTH: 231
<212> TYPE: PRT
<213> ORGANISM: Abdominal fat tissue from myoma uteri

<400> SEQUENCE: 2

Met Gly His Asp Gln Glu Thr Thr Thr Gln Pro Gly Val Leu Leu
 1               5                  10                  15

Pro Leu Pro Lys Gly Ala Cys Thr Gly Trp Met Ala Gly Ile Pro Gly
            20                  25                  30

His Pro Gly His Asn Gly Ala Pro Gly Arg Asp Gly Arg Asp Gly Thr
            35                  40                  45

Pro Gly Glu Lys Gly Glu Lys Gly Asp Pro Gly Leu Ile Gly Pro Lys
        50                  55                  60

Gly Asp Ile Gly Glu Thr Gly Val Pro Gly Ala Glu Gly Pro Arg Gly
65                  70                  75                  80

Phe Pro Gly Ile Gln Gly Arg Lys Gly Glu Pro Gly Glu Gly Ala Tyr
                85                  90                  95

Val Tyr Arg Ser Ala Phe Ser Val Gly Leu Glu Thr Tyr Val Thr Ile
                100                 105                 110

Pro Asn Met Pro Ile Arg Phe Thr Lys Ile Phe Tyr Asn Gln Gln Asn
            115                 120                 125

His Tyr Asp Gly Ser Thr Gly Lys Phe His Cys Asn Ile Pro Gly Leu
        130                 135                 140

Tyr Tyr Phe Ala Tyr His Ile Thr Val Tyr Met Lys Asp Val Lys Val
145                 150                 155                 160

Ser Leu Phe Lys Lys Asp Lys Ala Met Leu Phe Thr Tyr Asp Gln Tyr
                165                 170                 175

Gln Glu Asn Asn Val Asp Gln Ala Ser Gly Ser Val Leu Leu His Leu
            180                 185                 190

Glu Val Gly Asp Gln Val Trp Leu Gln Val Tyr Gly Glu Gly Glu Arg
        195                 200                 205

Asn Gly Leu Tyr Ala Asp Asn Asp Asn Asp Ser Thr Phe Thr Gly Phe
        210                 215                 220

Leu Leu Tyr His Asp Thr Asn
225                 230

<210> SEQ ID NO 3
<211> LENGTH: 29
<212> TYPE: DNA
<213> ORGANISM: PCR primer(forward) sequence for apM1

<400> SEQUENCE: 3
```

```
aacatatggg gcatgaccag gaaaccacg                                    29

<210> SEQ ID NO 4
<211> LENGTH: 29
<212> TYPE: DNA
<213> ORGANISM: PCR primer(reverse) sequence for apM1

<400> SEQUENCE: 4
aaggatcctc agttggtgtc atggtagag                                    29
```